United States Patent [19]

Osterweil

[11] Patent Number: 4,858,622
[45] Date of Patent: Aug. 22, 1989

[54] FALL ALERT SYSTEM WITH MAGNETICALLY OPERABLE SWITCH

[75] Inventor: Josef Osterweil, Rockville, Md.

[73] Assignee: J.D. Monitoring, Incorporated, Rockville, Md.

[21] Appl. No.: 32,675

[22] Filed: Apr. 1, 1987

[51] Int. Cl.⁴ .................................................. A61B 5/10
[52] U.S. Cl. ........................................ 128/782; 340/573
[58] Field of Search .................. 128/1 R, 774, 782; 340/539, 547, 548, 551, 568, 571, 573, 687

[56] References Cited

U.S. PATENT DOCUMENTS

| | | | |
|---|---|---|---|
| 3,887,909 | 6/1975 | Beiswenger et al. | 340/548 |
| 4,007,733 | 2/1977 | Celeste et al. | 128/2 |
| 4,160,972 | 7/1979 | La Mell et al. | 340/547 |
| 4,228,426 | 10/1980 | Roberts | 340/687 |
| 4,298,863 | 11/1981 | Natitus et al. | 128/782 |
| 4,389,635 | 6/1983 | Gallagher | 340/539 |
| 4,418,336 | 11/1983 | Taylor | 340/571 |
| 4,536,754 | 8/1985 | Holce et al. | 340/568 |
| 4,577,185 | 3/1986 | Andersen | 340/573 |
| 4,583,084 | 4/1986 | Henderson et al. | 340/573 |
| 4,616,113 | 10/1986 | Jank et al. | 340/568 |
| 4,638,307 | 1/1987 | Swartout | 340/573 |
| 4,639,713 | 1/1987 | Kitagawa et al. | 340/88 |

OTHER PUBLICATIONS

Specifier's Guide for Proximity Sensors, Micro Switch, a Honeywell Division, Catalog 50, Issue 5, pp. 111–113.

Primary Examiner—Max Hindenburg
Attorney, Agent, or Firm—Griffin, Branigan & Butler

[57] ABSTRACT

A fall alert system (100) for informing monitoring personnel at a remote location when a monitored person falls. In one embodiment, a monitoring device (120) is positioned proximate a bed. A harness (36), having a ferromagnetic shunt (34) at one end, is attached to the person to be monitored. While the person is lying in bed, the shunt (34) is attached to a sensing means (18). When the monitored person is about to fall out of bed, the shunt (34) detaches from the sensing means (18), alerting monitoring personnel. Another embodiment is disclosed for monitoring mobile persons that wander from room to room in a their home or facility.

9 Claims, 10 Drawing Sheets

A WILL BE RECEIVED AT TWO POINTS .33 λ APART
B WILL BE RECEIVED AT TWO POINTS .33 λ APART
C WILL BE RECEIVED AT THREE POINTS .2 λ APART

FALL ALERT SYSTEM WITH MAGNETICALLY OPERABLE SWITCH

BACKGROUND OF THE INVENTION

1. Field of the Invention

This invention relates to an apparatus for alerting monitoring personnel located at a remote site that a monitored person has fallen.

2. Prior Art and Other Considerations

A concern among the health care profession is that prompt attention be given to persons who fall. For example, an elderly person may collapse from a heart attack. It is essential to quickly reach such a stricken person if one is to save the person's life. In another instance, a person in a hospital bed or home for the aged may try to get out of the bed and fall. A nurse should return the fallen person to the bed and treat any injuries that were sustained.

In view of the above, it is an object of the present invention to provide a device which instantly transmits a signal to a remote site to alert monitoring personnel that a person is about to fall or has fallen.

An advantage of the present invention is the provision of apparatus that is easily interfaced to an existing facility's nurse calling system.

Another advantage of the present invention is the provision of apparatus that is adapatable for use in facilities that do not have any central paging systems, such as a home for the aged or an individual's home.

SUMMARY

A fall alert system for informing monitoring personnel at a remote location when a monitored person falls. In one embodiment, a monitoring device is positioned proximate a bed. A harness, having a shunt at one end, is placed on the person to be monitored. While the person is lying in bed, the shunt is attached to a sensing means. If the monitored person moves beyond a predetermined perimeter in the bed or falls out of bed, the shunt detaches from the sensing means, alerting the monitoring personnel. Another embodiment is disclosed for monitoring mobile persons that may wander from room to room in a facility.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DETAILED DESCRIPTION OF THE DRAWINGS

Figure 1:
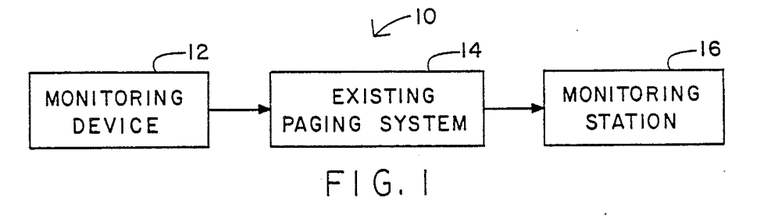
FIG. 1 is a diagrammatic view of a first embodiment of a fall alert system interfaced to a facility's existing central paging system.

A fall alert system 10 of the embodiment of FIG. 1 comprises a monitoring device 12, alerting means 14 (such as a facility existing paging system) and a monitoring station 16.

Figure 8:
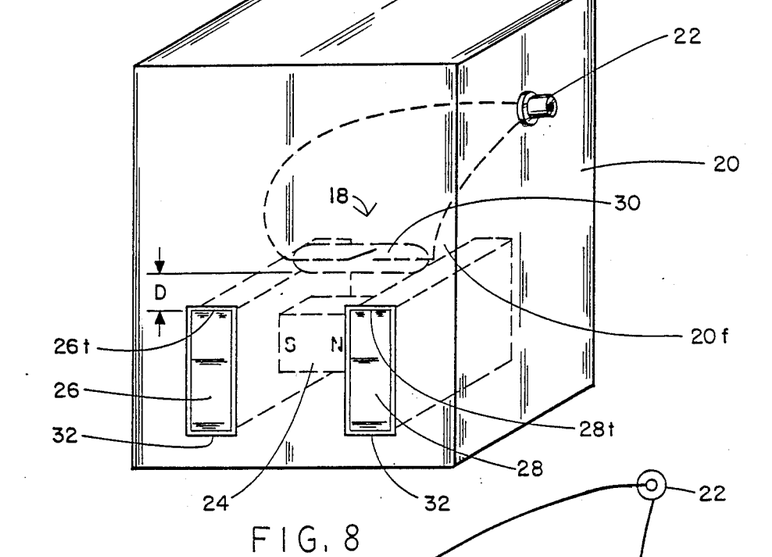
FIG. 8 is an isometric view illustrating a sensing means used in various embodiments of the invention, the sensing means being housed in an enclosure.

Monitoring device 12 is further illustrated in FIG. 8 as comprising a sensing means 18, mounted in an enclosure 20. Enclosure 20 has a central paging interfacing means, such as a phono jack 22.

Figure 9:
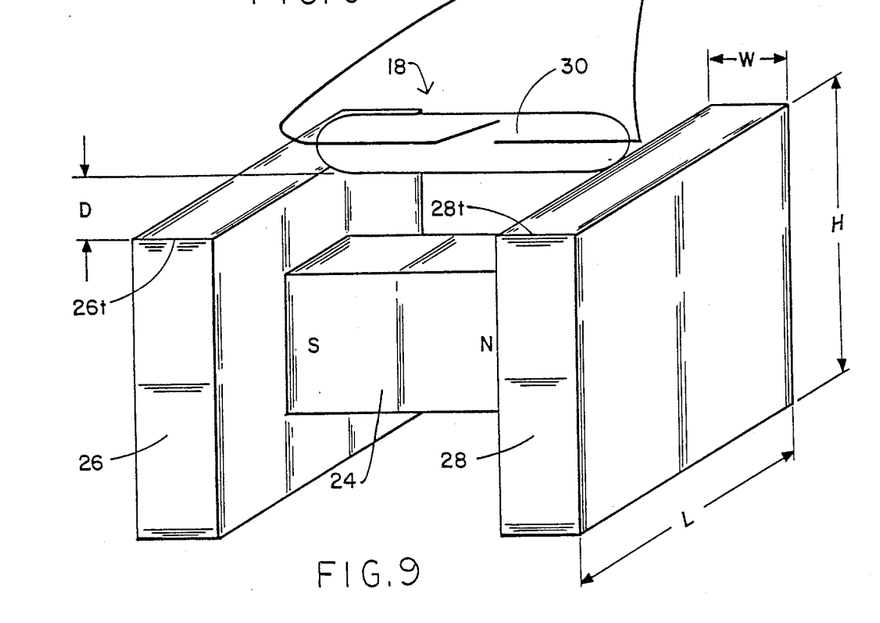
FIG. 9 is an isometric view illustrating the sensing means of FIG. 8 unobscured by its enclosure.

As shown in FIG. 9, the sensing means 18 comprises a source of magnetic field, such as a magnet 24. A first magnetic field directing means 26 is placed substantially perpendicular and adjacent to the south magnetic pole of the magnet 24. A second magnetic directing means 28 is similarly placed substantially perpendicular and adjacent to the north magnetic pole of the magnet 24. The first and second magnetic directing means 26, 28 are fabricated from a material possessing ferromagnetic properties, such as a strip of iron. In a preferred embodiment, the strip of iron 26, 28 is substantially rectangular, having a length L, a height H and a width W. Output state changing means, such as a magnetically operated switch or a reed switch 30, is positioned proximate a front wall 20f of the enclosure 20 a predetermined distance D above tops 26t, 28t of the magnetic directing means 26,28 and substantially parallel to the north-south pole of the magnet 24. The reed switch 30 is connected to the phono jack 22. The reed switch 30 detects the presence or absence of a magnetic field created by the magnet 24. In the presence of the magnetic field, the output of the reed switch changes from a first state to a second state.

Enclosure 20 is provided with two substantially parallel openings 32. The openings 32 are formed so as to be slightly greater than the height H and width W of the directing means 26, 28. The sensing means 18 is positioned in the enclosure 20 such that a portion of one end of each directing means 26, 28 protrudes through the openings 32 for engaging an activating means, such as a magnetic shunt 34 (see FIG. 10). In a preferred embodiment, the shunt 34 is a circular washer manufactured from a ferromagnetic material, such as iron. The particular shunt 34 selected must be able to redirect the magnetic field of the magnet 24 through the shunt 34. A harness 36, to be discussed below, is attached to the shunt 34.

The operation of the sensing means 18 is based on the presence and absence of a magnetic field. When the ferromagnetic shunt 34 is placed across the directing means 26,28, the magnetic field in the periphery of the poles is reduced. That is, the majority of the magnetic flux will be concentrated in the shunt 34. The reed switch 30 is positioned in a location that exhibits a significant reduction in the magnetic field as a result of the presence of the shunt 34 against the magnetic poles of the magnet 24. Accordingly, the magnetic field of the magnet 24 has no effect on the reed switch 30. When the shunt 34 is removed from the magnet, the strength of the magnetic field at the location of the reed switch increases. The increase of the magnetic field causes the output of the reed switch 30 to change to the second output state.

Figure 11:
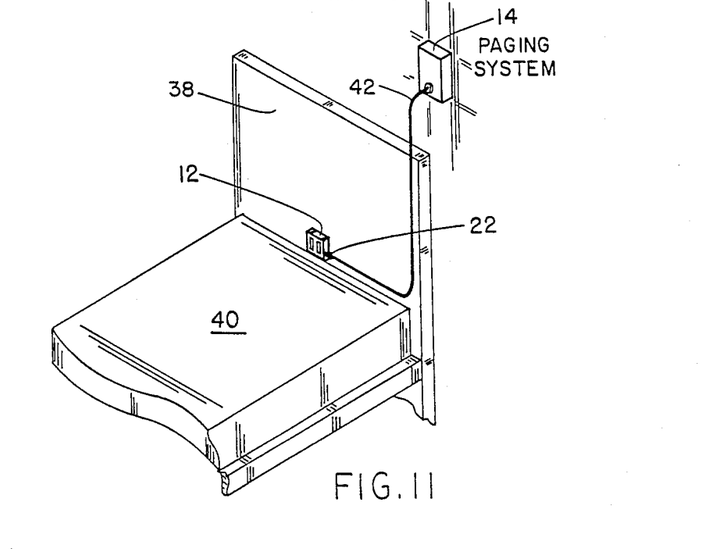
FIG. 11 is an isometric view illustrating the fall alert system adapted for use with a bed.

A typical use of the first embodiment is in a facility wherein each bed is equipped with a paging system 14. As shown in FIG. 11, the monitoring device 12 is placed against a headboard 38 of a bed 40. If a headboard is not available, the monitoring device is attached to a wall. An interconnect cable 42 has one end plugged into the existing paging system 14 while the other end of the interconnect cable 42 is plugged into the phono jack 22 on the monitoring device 12. If desired, an auxillary jack (not shown) can be provided in parallel with the phono jack 22 so that a patient calling switch (which would normally be plugged into the paging system 14) can still be used.

If necessary, plural reed switches can be employed along with suitable modifications to the interconnect cable 42 and phono jack 22) to adapt the monitoring device to paging systems that require multicontact switch closures to operate.

Figures 12, 13A, 13B, 13C:
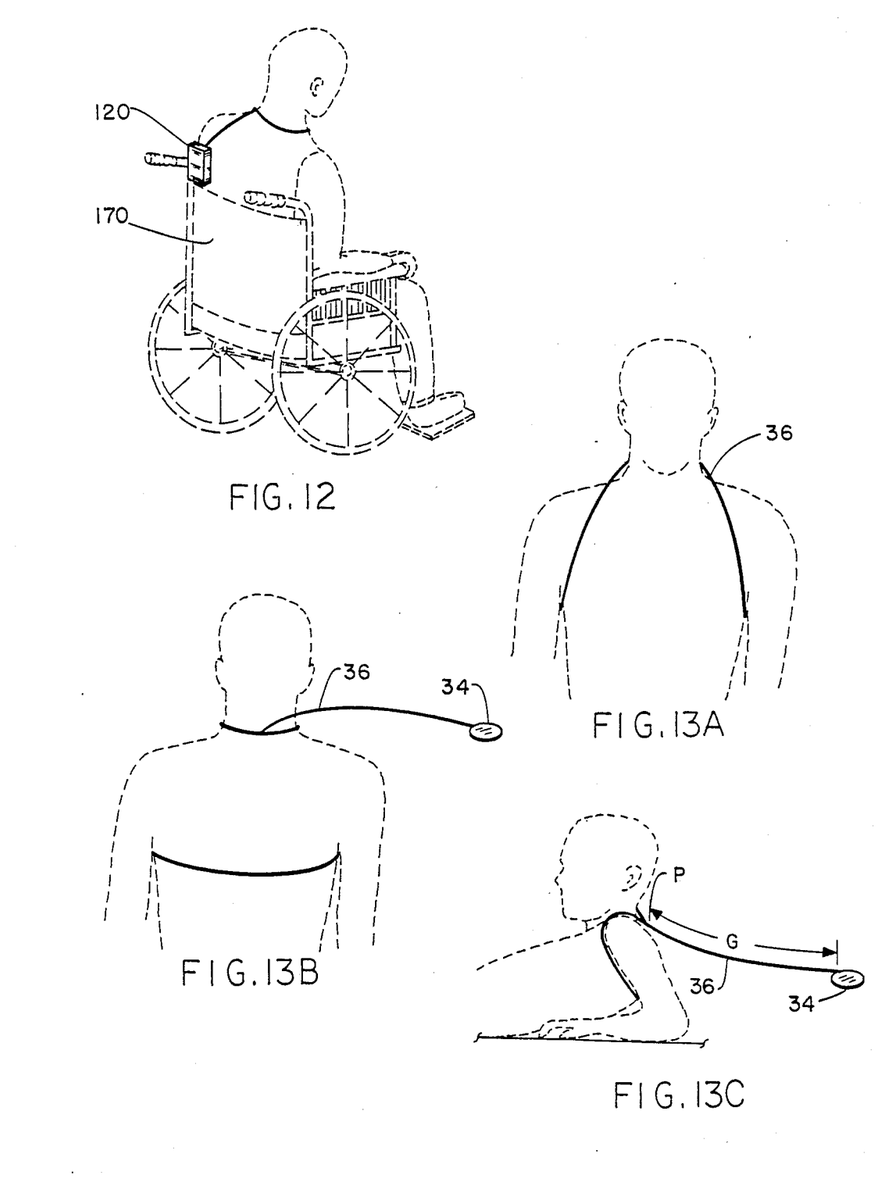
FIG. 12 is an isometric view illustrating the invention adapted for use with a wheelchair.
FIG. 13(A), 13(B), and 13(C) are front, rear, and side views, respectively of a harness worn by a person confined to a bed or wheelchair.

As shown in FIGS. 13, the preferred harness 36 comprises a strip of flexible material having one end wrapped around the upper portion of the back of the person to be monitored, passing underneath his arms (FIG. 13B) towards his front torso and then upwards towards the back of his neck (FIG. 13A) for attachment to the flexible material at an attachment point P. The harness 36 continues for a predetermined distance G after point P for connection to the shunt 34 (FIG. 13C). The harness is comfortable to wear, but will not accidentally fall off the wearer. An alternative harness 36 has been constructed in which the harness 36 is attached to the person's garment by the use of a clip.

Figure 10:
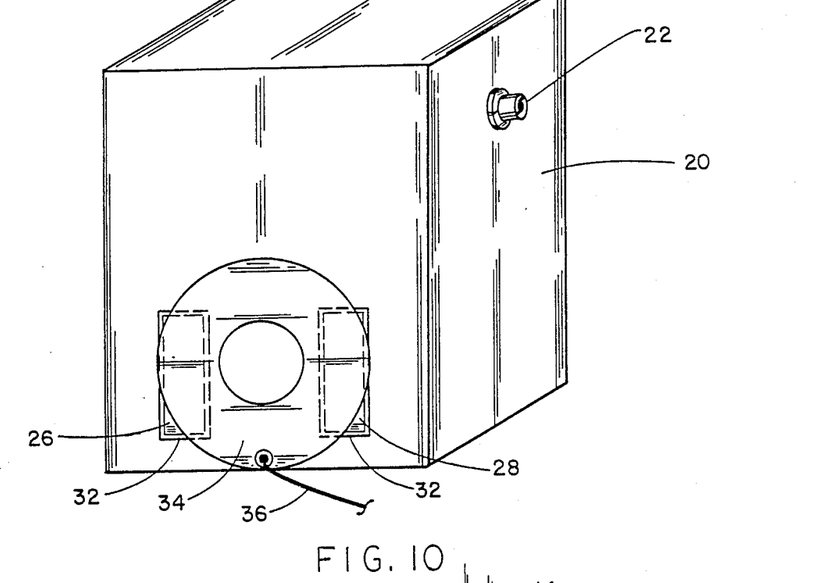
FIG. 10 is an isometric view illustrating an activation means used with the sensing means of in FIG. 8.

With the patient lying in the bed 40, a nurse or other assistant secures the shunt 34 to the magnetic directing means 26, 28 of the monitoring device 12 as shown in FIG. 10. As long as the patient remains in bed, the shunt 34 remains in contact with the directing means 26, 28. During this period of time, the magnetic field of the magnet 24 is directed from the north pole of the magnet 24, through the directing means 28, shunt 34, directing means 26 and finally to the south pole of the magnet 24. If the patient falls out of bed (or attempts to get out of the bed), the shunt 34 separates from the monitoring device 12. When this occurs, the magnetic field of the magnet flows through the reed switch 30, causing the output of the reed switch 30 to change from its initial first state to its second state. When the reed switch 30 changes to the second state, a closed circuit is created in the central paging system 14, activating an indicator at the monitoring station 16 to alert monitoring personnel that the monitored person is no longer in bed.

Figure 2:
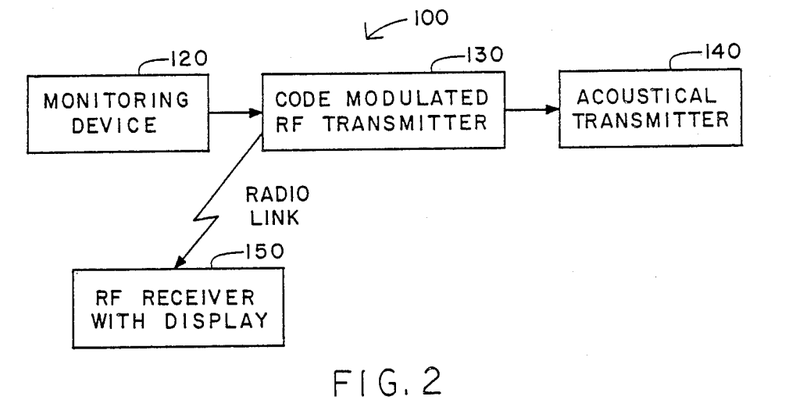
FIG. 2 is a diagrammatic view of a second embodiment of the invention for use in a facility which does not have a central paging system.

Many facilities, such as an individual's home or a home for the aged, do not have a central paging system. In these environments, the second embodiment shown in FIG. 2 is used. In this embodiment, the fall alert system 100 comprises a monitoring device 120, a transmitter, such as a code modulated RF transmitter 130, an acoustical transmitter 140 and a receiver/display unit, such as a code modulated RF receiver/display unit 150. The monitoring device 120 is constructed in a similar fashion to the monitoring device 12 of the first embodiment. However, also housed inside the enclosure 20 is the code modulated RF transmitter 130 and acoustical transmitter 140. The specific construction of the code modulated RF transmitter 130 and acoustical transmitter 140 is well known to those skilled in the art, typically being used in the security community, and will not be discussed herein.

Figure 7A:
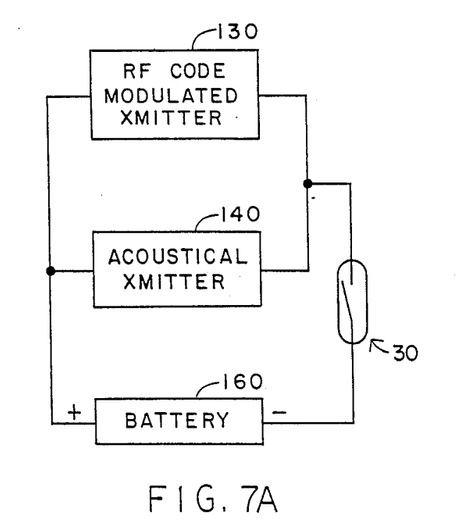
FIG. 7A is a diagrammatic view of a typical electrical hook-up of a transmitting portion of the fall alert system used in the second embodiment.

As shown in FIG. 7A, one lead of the reed switch 30 is connected to the negative terminal of a battery 160. The remaining lead of the reed switch 30 is connected to the corresponding negative power leads of the transmitters 130, 140. The positive terminal of the battery 160 is connected to the corresponding power lead of the transmitters 130, 140. When the reed switch 30 is in its first state, an open circuit exists. Thus, there is no current drain on the battery 160 until the reed switch 30 changes to its second output state. Alternative embodiments can be constructed in which the closure of the reed switch 30 activates a power enable pin of an electronic circuit, switching the circuit from a stand-by mode to a power-on mode.

The same harness 36 and shunt 34 used with the first embodiment is used with the second embodiment. If the monitored person attempts to leave the bed or actually falls out of bed, the shunt 34 separates from the monitoring device 120 causing the magnetic field of the magnet 24 to flow through the reed switch 30, causing the output of the reed switch 30 to change from its initial first output state to its second output state. The output state change of the reed switch 30 results in the transmitters 130, 140 being supplied with electrical power and becoming operational. As noted above, the RF transmitter 130 transmits a coded signal to the RF receiver/display unit 150. This permits one receiver to be used with a plurality of monitoring devices. When the RF receiver 150 detects a signal from the RF transmitter 130, a display or other indicator is activated to alert the monitoring personnel that an individual may have fallen. The indicator on the RF receiver 150 alerts the monitoring personnel to the general vicinity of the fallen individual. As the monitoring personnel approach the fallen person, they can determine the exact location by tracking the sound generated by the acoustical transmitter 140.

The second embodiment is also usable with a wheelchair 170 as shown in FIG. 12. The monitoring device 120 is attached to the back of the wheelchair 170. If the monitored person gets out of the wheelchair, falls out of the wheelchair, or excessively slouches so that he may fall out of the wheelchair, the transmitters 130, 140 are activated in the same manner as described above.

Figure 16:
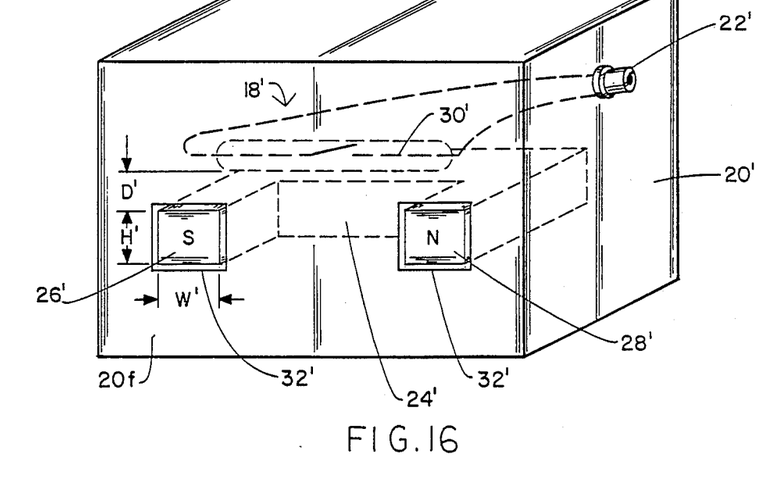
FIG. 16 is an isometric view illustrating an alternative sensing means used in various embodiments of the invention, the sensing means being housed in an enclosure.
Figure 17:
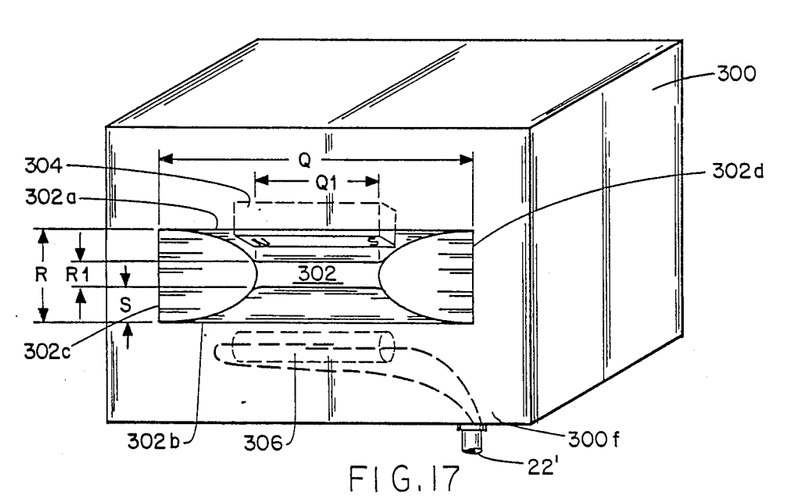
FIG. 17 is an isometric view illustrating a slotted sensing means used in various embodiments of the invention.
Figure 18:
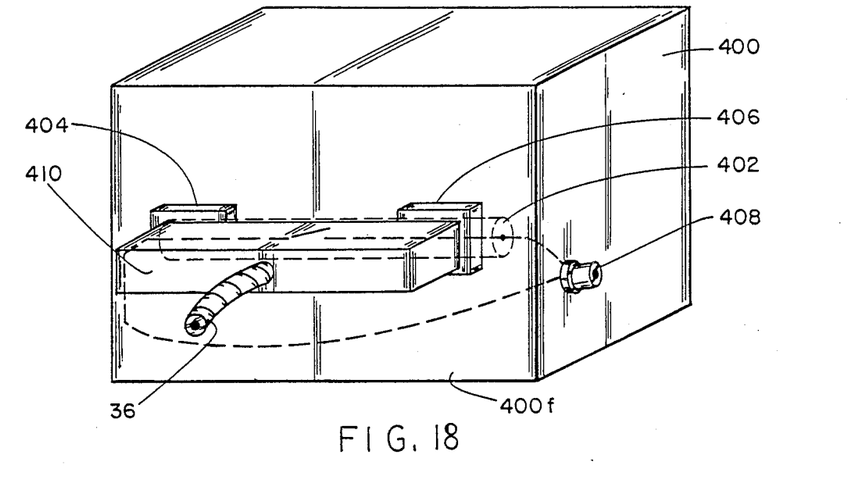
FIG. 18 is an isometric view illustrating another sensing means that is usable with various embodiments of the invention.

FIGS. 16, 17 and 18 illustrate alternative sensing means that may be utilized with the first and second embodiments.

In FIG. 16, a source of magnetic field is substantially U-shaped, such as a U-shaped magnet 24'. The magnet 24' has a first magnetic field directing pole 26' and a second magnetic field directing pole 28'. The first and second poles 26' and 28' have a width W' and a height H'. The magnet 24' is housed inside an enclosure 20', a portion of the two directing poles 26',28' protruding through two substantially parallel openings 32' in a front wall 20f' of the enclosure 20'. The dimensions of the openings 32' are slightly greater than the height H' and width W' of the two directing poles 26', 28'. Output state changing means, such as a reed switch 30' is positioned inside the enclosure 20' proximate the front wall 20f' of the enclosure 20' a predetermined distance D' above the top surface of the magnetic poles 26', 28' and substantially parallel to the magnet 24'. The reed switch is then connected to a central paging interfacing means, such as a phono jack 22' (or alternatively to a transmitter) as discussed above.

A slotted enclosure magnetic sensor is illustrated in FIG. 17. An enclosure 300 is manufactured from a non-ferromagnetic material, such as plastic. A substantially rectangular slot 302 is formed in a front wall 300f of the enclosure 300. The slot 302 has two sides 302a,302b of length Q and two sides 302c,302d of length R in the front wall 300f. The slot 302 has a depth S. At depth S, the rectangular slot 302 is smaller, having a length Q1 with respect to sides 302a,302b and a length R1 with respect to sides 302c,302d. This gives the rectangular slot 302 a quasi-conical appearance. A source of magnetic field, such as a magnet 304 is secured inside the enclosure 300 at a selected point along the slot's depth S proximate side 302a. An output state changing means, such as a reed switch 306, is positioned inside the enclosure 300 substantially parallel to and in the same plane as the magnet 304 but proximate the side 302b of the enclosure 302. The reed switch is interfaced to the remaining circuitry as described above.

In use, the shunt 34 described above is dropped into the slot 302 such that the shunt 34 is proximate the magnet 304. This results in the magnetic field of the magnet 304 being concentrated in the shunt 34. The size of the slot 302 is greater than the size of the shunt 34 so that the shunt 34 may be easily inserted into the slot 302 and also pulled out from all directions. When a monitored person is about to fall, the shunt 34 is pulled out of the slot 302. The magnetic field of the magnet 304 then passes through the reed switch 306, causing the output of the reed switch to change from a first state to a second state This output state change activates associated circuitry which alerts monitoring personnel that a person has fallen.

FIG. 18 illustrates a fourth type of magnetic sensor. An enclosure 400 is manufactured out of plastic or other non-ferromagnetic material. An output state changing means, such as a reed switch 402, is secured to the inside surface of a front wall 400f of the enclosure 400. A first magnetic field directing means 404 and a second magnetic field directing means 406 are secured to the outside of the front wall 400f proximate each end of the reed switch 402. The directing means 404,406 are manufactured from a ferromagnetic material, such as iron. The reed switch 402 is connected to a phono jack 408 for interfacing to a paging system, or alternatively, connected to a transmitter as described above.

The harness 36 used in the above-embodiments is employed with the fourth type of magnetic sensor. However, a source of magnetic field, such as a magnet 410, is substituted for the shunt 34.

When the magnet 410 is in contact with the directing means 404,406, the output of the reed switch 402 is in a first state. When a monitored person is about to fall, the magnet 410 is pulled away from the directing means 404,406. This causes the output of the reed switch 402 to change to a second state, activating circuitry which alerts monitoring personnel that a person has fallen.

The construction of the various magnetic sensors above permit the shunt 34 (or magnet 410 of the fourth type of magnetic sensor) to be easily pulled away from the sensor in any direction.

The two embodiments described above are primarily intended for persons confined to an object such as a bed, chair, or wheelchair. In situations where the person-to-be-monitored is not so confined, i.e. able to move from one location to another, third and fourth embodiments, described below, are usable.

In the third embodiment (FIG. 3), fall alert system 200 comprises a monitoring device 210, a transmitter, such as a double-tone acoustical transmitter 220, and a receiver, such as a double-tone acoustical receiver 230 which is interfaced to a facility's existing paging system 240.

Figure 14:
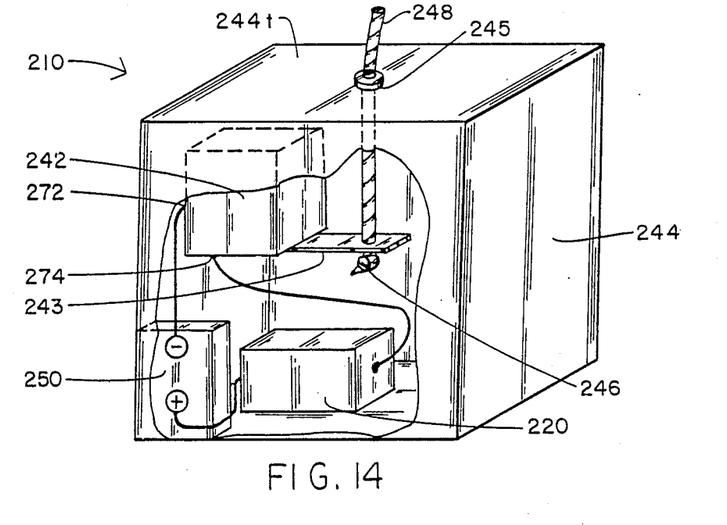
FIG. 14 is an isometric view, partially cutaway, of an alternative sensing means for use with a mobile person.
Figure 15:
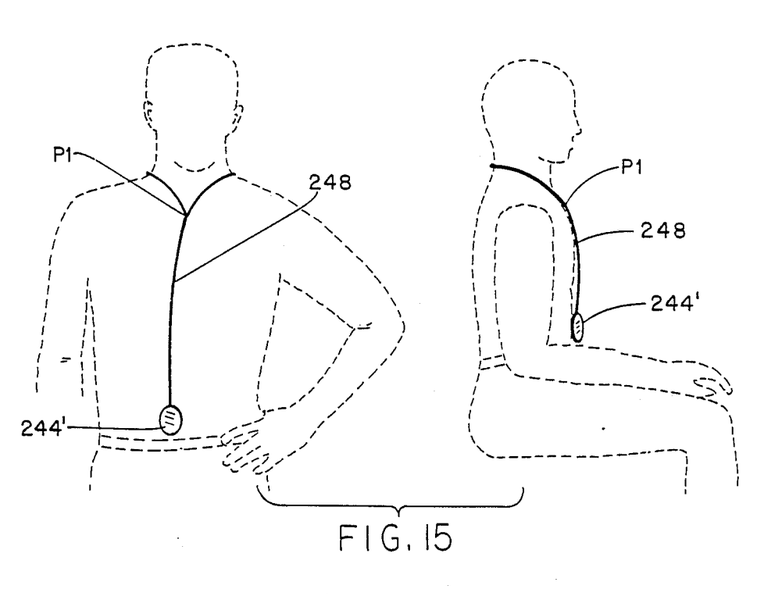
FIG. 15 are front and side views, respectively, of a person standing and sitting wearing the alternative sensing means of FIG. 14.

The monitoring device 210 is illustrated in FIG. 14 as comprising an enclosure 244 containing a sensing means 242, the acoustical double-tone transmitter 220, and a battery 250. The shape of the enclosure 244 is not critical. In this regard, in FIG. 14 a substantially rectangular enclosure 244 is shown while in FIG. 15 a substantially circular enclosure 244' is shown. The only requirement as to the size and shape of the enclosure is that it be of sufficient volume to house the associated electronics.

The sensing means 242 comprises a tension sensing transducer which may be mechanical, pizoelectric, magnetic or solid state. In a preferred embodiment, the sensing means 242 comprises a normally closed, momentary lever-type switch 242 having a first output state and a second output state. The switch 242 is mounted upside-down and has a lever 243 that is substantially parallel to a top surface 244t of the enclosure 244. A free end of the lever 243 on the switch 242 is aligned with an opening 245 in the top surface 244t. A free end 246 of a harness 248, to be discussed below, passes through the opening 245 in the top surface 244t and is secured to the free end of the lever 243 of the switch 242 for controlling the output of the switch 242.

Figure 7B:
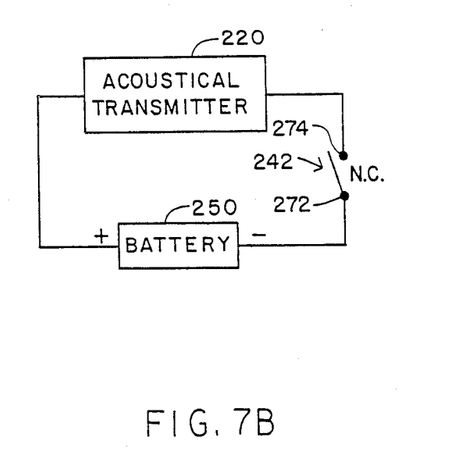
FIG. 7B is a typical diagrammatic view of a transmitting portion of the fall alert system employed in the third embodiment of the invention.

As shown in FIG. 7B and FIG. 14, one terminal 272 of the lever switch 242 is connected to the negative terminal of the battery 250. Remaining terminal 274 of the switch 242 is connected to the power lead of the acoustical transmitter 220. The positive terminal of the battery 250 is connected to the positive power lead of the transmitter 220. When the harness 248 is under tension, the switch 242 is in its first output state, resulting in an open electrical circuit. As will be further discussed below, when tension in the harness 248 is eliminated, the output of the switch 242 changes to its second state, completing the electrical circuit and activating the acoustical alarm 220.

The construction of the double-tone acoustical transmitter 220 is also known to one skilled in the art. The two tones are selected so as not to be multiples of each other. Additionally, the two tones are selected so as not to be similar to the typical types of sounds found in the facility the device is to be used. These precautions are taken so as to reduce the likelihood of false triggering.

Figure 5:
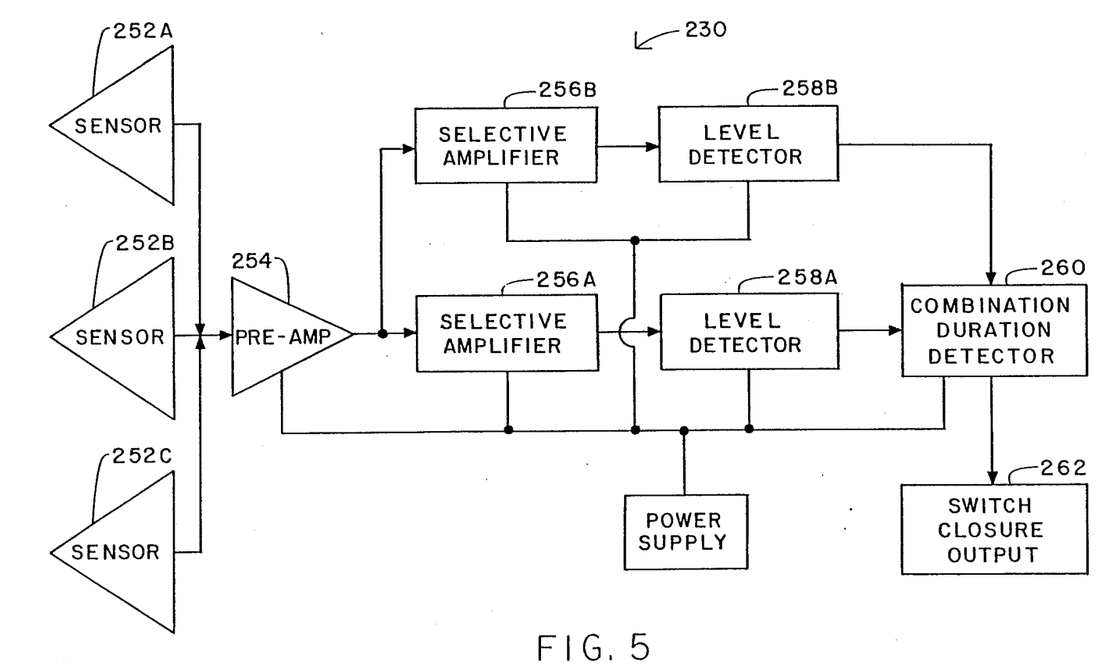
FIG. 5 is a diagrammatic view of an acoustical double-tone receiver employed in the embodiments of FIGS. 3 and 4.
Figure 6:
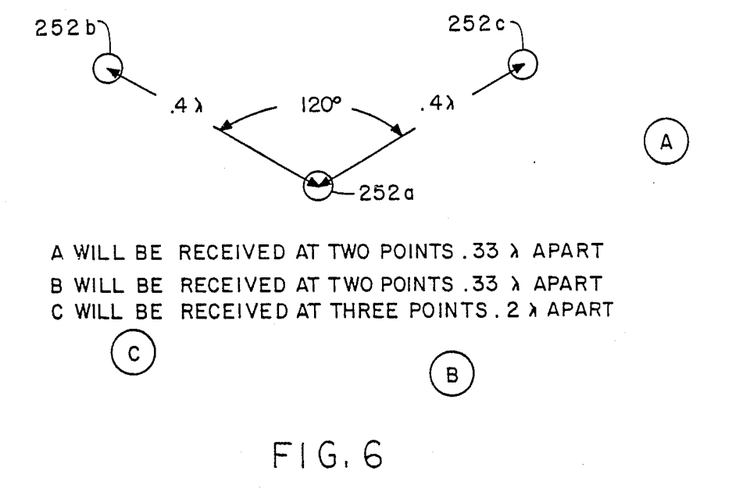
FIG. 6 is a diagrammatic view displaying a spatial relationship of three audio sensor pickups used with the acoustical double-tone receiver illustrated in FIG. 5.

The acoustical double-tone receiver 230 employed in the preferred embodiment is understood with reference to FIGS. 5 and 6. As shown in FIG. 6, a first audio sensor pickup 252A is positioned at a point in a room. Second and third audio sensor pickups 252B, 252C are each placed 4/10 of a wavelength away from the first sensor 252A so as to form a 120 degree angle between pickups 252B, 252C. If two monitoring devices are triggered in the monitored room, phase cancellation of the transmitted signal can result. The chosen space diversity of the audio sensors 252 is selected to ensure that at least one of the audio sensors 252 receive a correct signal.

Figure 3:
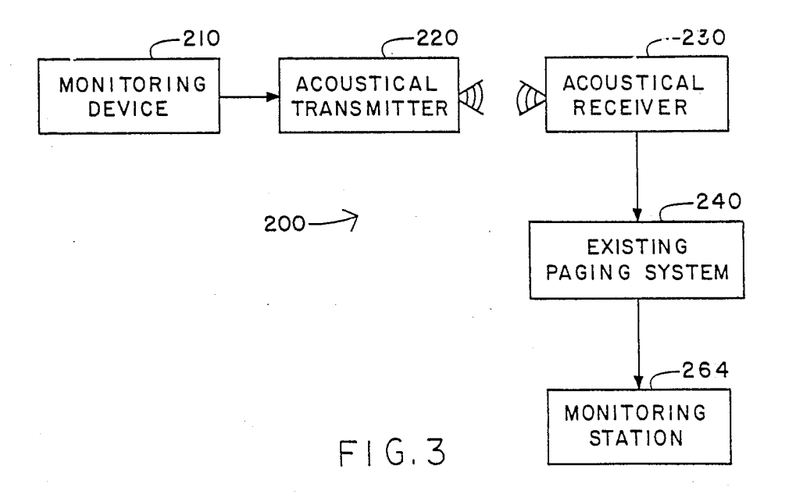
FIG. 3 is a diagrammatic view of a third embodiment of the invention for use in a facility having a central paging system for monitoring mobile persons.

The double-tone signal detected by the sensors 252 is amplified by preamplifier 254. The amplified double-tone signal is inputted to two selective amplifiers 256A, 256B which amplify only a specific portion of the frequency spectrum. This results in two distinct output signals. Each output signal is inputted to an associated level detector 258A, 258B and to a combination/duration detector 260. If the double tone signal produced by the transmitter 220 matches the tuning of the receiver 230, detection switch 262 in the receiver 230 is activated. The detection switch 262 is interfaced to the facility's existing paging system 240 by an interconnection cable (not shown). The activation of switch 262 completes an electrical circuit in the paging system 240, alerting monitoring personnel stationed at monitoring station 264 (FIG. 3). The double-tone receiver 230 may be constructed using discrete components or using commercial dual-tone multi-frequency decoders (DTMF), such as an MV8870 DTMF receiver manufactured by Plessey Semiconductors. It is understood that a power source, either from an AC line, battery or combination of the two, is used to power the receiver 230.

The harness 248 comprises a strip of flexible material having one end wrapped around a person's neck and secured at a point P1 between its free ends. The opposite end of the flexible material is secured to the switch 242, as noted above. The harness 248 is worn such that the monitoring device is proximate the wearer's front torso. With the person standing or sitting (FIG. 15), the weight of the enclosure 244 and associated electronics creates a tension in the harness 248, causing the switch 242 in the enclosure 244 to be in an open, first output state position. If the person falls, the tension in the harness 248 is eliminated. When this occurs, the output of the switch 242 changes to its second output state, supplying electrical power to the acoustical transmitter 220. The transmitter 220 produces an audible signal which is recognized by the receiver 230 to activate an indicator at the monitoring station 264. Monitoring personnel can then rush to the fallen person and render assistance.

Figure 4:
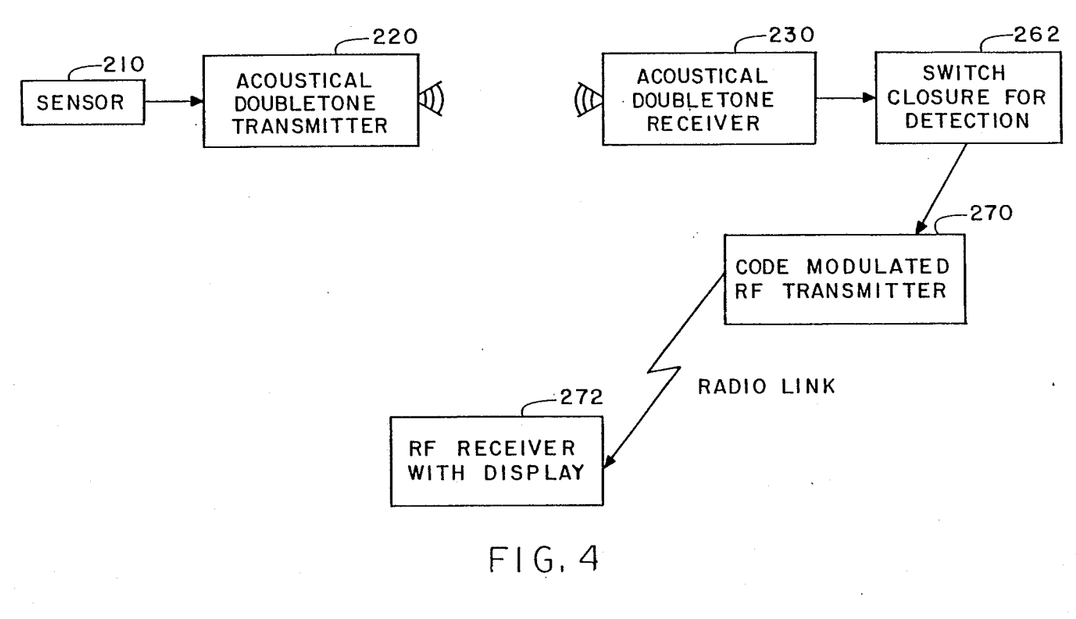
FIG. 4 is a diagrammatic view of a fourth embodiment of a fall alert system for use in a facility not having a central paging system for monitoring mobile persons.

A fourth embodiment is provided for facilities which do not have a central paging system. This embodiment (FIG. 4) is actually a variation of the third embodiment with the code modulated transmitter/receiver of the second embodiment. The detection switch 262 in the receiver 230 is interfaced to a code modulated RF transmitter 270. When a person falls, the acoustical receiver 230 activates the code modulated RF transmitter 270, which transmits the signal to an RF receiver/display unit 272.

While the invention has been particularly shown and described with reference to the preferred embodiments thereof, it will be understood by those skilled in the art that various alterations in form and detail may be made therein without departing from the spirit and scope of the invention. For example, an infrared, ultrasonic or radio frequency transmitter/receiver could be substituted for the coded RF transmitter/receiver. A Hall effect solid state device or similar sensor may be substituted for the reed switch. Alternatively, a telephone dialing and message unit could be interfaced to the apparatus to alert monitoring personnel monitoring aged or infirm people residing in their own home.

The embodiments of the invention in which an exclusive property or privilege is claimed are defined as follows:

1. A human monitoring device for alerting monitoring personnel located at a remote location that a monitored person may have fallen, said device comprising:
   (a) an enclosure, said enclosure being manufactured from a non-ferromagnetic material and having an opening in one wall;
   (b) a source of magnetic field secured inside said enclosure proximate a first side of said opening in said enclosure;
   (c) a magnetically operable switch secured inside said enclosure proximate a second side of said opening in said enclosure, said magnetically operable switch being positioned so that it is substantially parallel to said source of magnetic field, the output of said magnetically operable switch changing from a first state to a second state in the presence of said magnetic field;
   (d) shunting means selectively positioned between said source of magnetic field and said magnetically operable switch, said shunting means operating to divert said source of magnetic field away from said magnetically operable switch;
   (e) a harness having two ends, one end of said harness being attached to said shunting means, the remaining end of said harness being secured to said monitored person in a manner whereby said shunting means is withdrawn from said opening in said enclosure if said monitored person exceeds a predetermined range of movement with respect to said monitoring device, said movement causing said magnetically operable switch to change to said second state; and,
   (f) alerting means for sending a signal to said remote location when said magnetically operable switch changes from said first state to said second state to alert said monitoring personnel that said monitored person may have fallen.

2. The device of claim 1, wherein said magnetically operable switch comprises a reed switch.

3. The device of claim 1, wherein said opening in said enclosure is quasi-conical in shape to facilitate the removal of said shunting means from said enclosure.

4. A human monitoring device as recited in claim 1, wherein said alerting means comprises a radio transmitter and a radio receiver, said signal being coded to facilitate the identification of said monitored person.

5. The device of claim 1, wherein said alerting means comprises a central paging system.

6. The device of claim 1, further comprising:
   locating means housed in said enclosure for providing an indication of the location of said monitored person.

7. The device of claim 6, wherein said alerting means comprises a radio transmitter and a radio receiver, said signal being coded to facilitate the identification of said monitored person.

8. The device of claim 6, wherein said alerting means comprises a signal audibly transmitted to an associated receiver when the output of said sensing means changes to said second state.

9. The device of claim 8, wherein said audible signal comprises a plurality of distinct signals mixed together.

* * * * *